United States Patent [19]
Schelhas

[11] Patent Number: 5,427,586
[45] Date of Patent: Jun. 27, 1995

[54] KNEE-JOINT ENDOPROSTHESIS

[75] Inventor: Klaus D. Schelhas, Harpstedt, Germany

[73] Assignee: Ingrid Schelhas, Harpstedt, Germany

[21] Appl. No.: 109,700

[22] Filed: Aug. 20, 1993

Related U.S. Application Data

[63] Continuation of Ser. No. 879,609, May 7, 1992, abandoned.

[51] Int. Cl.⁶ ............................................. A61F 2/38
[52] U.S. Cl. ............................................. 623/20
[58] Field of Search ......................... 623/16, 18, 20

[56] References Cited

U.S. PATENT DOCUMENTS

| | | | |
|---|---|---|---|
| 3,748,662 | 7/1973 | Helfet | 623/20 |
| 3,837,009 | 9/1974 | Walker | 623/20 |
| 3,868,730 | 3/1975 | Kaufer et al. | 623/20 |
| 4,094,017 | 6/1978 | Matthews et al. | 623/20 |
| 4,136,405 | 1/1979 | Pastrick et al. | 623/20 |

Primary Examiner—David Isabella
Attorney, Agent, or Firm—Merchant & Gould, Smith, Edell, Welter & Schmidt

[57] ABSTRACT

A knee-joint endoprosthesis includes a femoral part having, at the lower end, two condylar pans, and a tibial part having a tibial plateau with upper support areas for supporting, and also for guiding the condylar pans with movements of the knee joint. The condylar pans each have a downwardly-running lateral wall, which, at its convexly-curved lower end passes over into a support surface running transversely outwardly. The condylar pans each have, ventrally at the transition from the lateral wall to the support wall, a recess directed toward inside of the pan, across which an intervening space between the condylar pans is widened such that, with stronger bending, the knee cap can enter into this widened zone of entry of the intervening space.

11 Claims, 5 Drawing Sheets

KNEE-JOINT ENDOPROSTHESIS

This is a continuation of application Ser. No. 07/879,609, filed May 7, 1992, now abandoned.

BACKGROUND OF THE INVENTION

The invention concerns a knee-joint endoprosthesis whose femoral part displays, at the lower end, two condylar pans, and whose tibial part displays a tibial plateau, with each condylar pan displaying a downwardly-running lateral wall, and a supporting wall running outwardly from the lateral wall for resting against the tibial plateau. These types of knee-joint endoprostheses are, for example, known as axle-free endoprostheses or, from DE 40 02 424 A1, in the form of so-called axle-knee endoprostheses. Shaping and dimensioning of the known-type, knee-joint endoprostheses allows for achieving an exact-as-possible imitation of the statics and mechanics of the natural knee joint—with a simple construction of the prosthesis. However, it has been shown that, short term or long term, after implantation of a known-type, knee-joint endoprosthesis, pain then frequently appears when the knee cap and corresponding ligamentous apparatus are preserved at the time of implantation.

It is further known to join the support areas of the two condylar pans ventrally and to lengthen them upwardly such that the ventral tip of the support areas covers the natural condyles in a region in which, with a bending movement, the patella (knee cap) comes to rest under pressure against the condyles. In the case of this known endoprosthesis, the knee cap lies against the smooth surface of the drawn-up support areas and not against the natural condyles. However, it has been shown that even the realization of a patella counter support of this type can not always prevent the difficulties appearing in the region of the knee cap with longer-term usage of the prosthesis.

SUMMARY OF THE INVENTION

Therefore, the object of the invention is to develop further the knee-joint endoprosthesis of the initially-mentioned variety in such a manner that the danger of difficulties in the region of the knee cap will be reduced, or even be completely eliminated.

In the case of the knee-joint endoprosthesis of the initially-mentioned variety, this objective is satisfied in accordance with the invention by the fact that the condylar pans display, ventrally, at the transition from the lateral wall to the supporting wall a recess directed toward the inside of the pan.

The advantages of the invention lie particularly in the fact that the recesses formed in the ventral region of the condylar pans provide space between the condylar pans for the knee cap, so that, with a bending movement, the knee cap can go between—and not in front of, like in the case of known prostheses—the support areas of the condylar pans, whereby the ligaments holding the knee cap shorten and can thereby relax. Assured by this that the pressure, or a patella counter support pressure from the knee cap acting upon the condyles with a bending movement, the so-called patella pressure, does not exceed a certain measure even with a strong bending of the knee joint, and—like in the case of the natural knee joint—even after exceeding a bend angle of 90° again decreases.

Particularly preferred, the recesses run from ventrally for a predetermined stretch to dorsally, with the depth of the recess, in particularly-preferred fashion, continually decreasing. The recesses end ahead of that dorsal region of the support walls that remains in supporting contact with the support surfaces of the tibial plateau, even in the case of stronger bending. The recesses at the transition between lateral walls and support walls of the condylar pans have a depth such that the knee cap—with increasing bending of the joint—can run into the free (open) space between the condylar pans that is produced by the recesses. Preferably, the recesses are dimensioned such that the knee cap—in the case of strong bending movements—lies, and/or can be guided laterally, with its lateral zones lying lightly against the recessed surfaces of the condylar pans.

According to a preferred form of embodiment of the invention, the support areas of the tibial plateau contain bulges that correspond to the recesses and that run in the ventral/dorsal direction. Here, the bulges support a protuberance running dorsally/ventrally, possibly between the support areas when guiding the movement of the condylar pans, when the femoral part and the tibial part are brought into an extended position.

Particularly preferred, the recesses are provided in the case of knee-joint endoprostheses where tibial part and femoral part are joined in articulated fashion with one another by means of a connecting part and/or a transverse pin.

These and various other advantages and features of novelty which characterize the invention are pointed out with particularity in the claims annexed hereto and forming a part hereof. However, for a better understanding of the invention, its advantages, and objects obtained by its use, reference should be had to the drawing which forms a further part hereof, and to the accompanying descriptive matter, in which there is illustrated and described a preferred embodiment of the invention.

BRIEF DESCRIPTION OF THE DRAWINGS

Explained in more detail in the following with the aid of the drawing are examples of embodiment of the invention.

DETAILED DESCRIPTION OF THE PREFERRED EMBODIMENT

Figure 1:
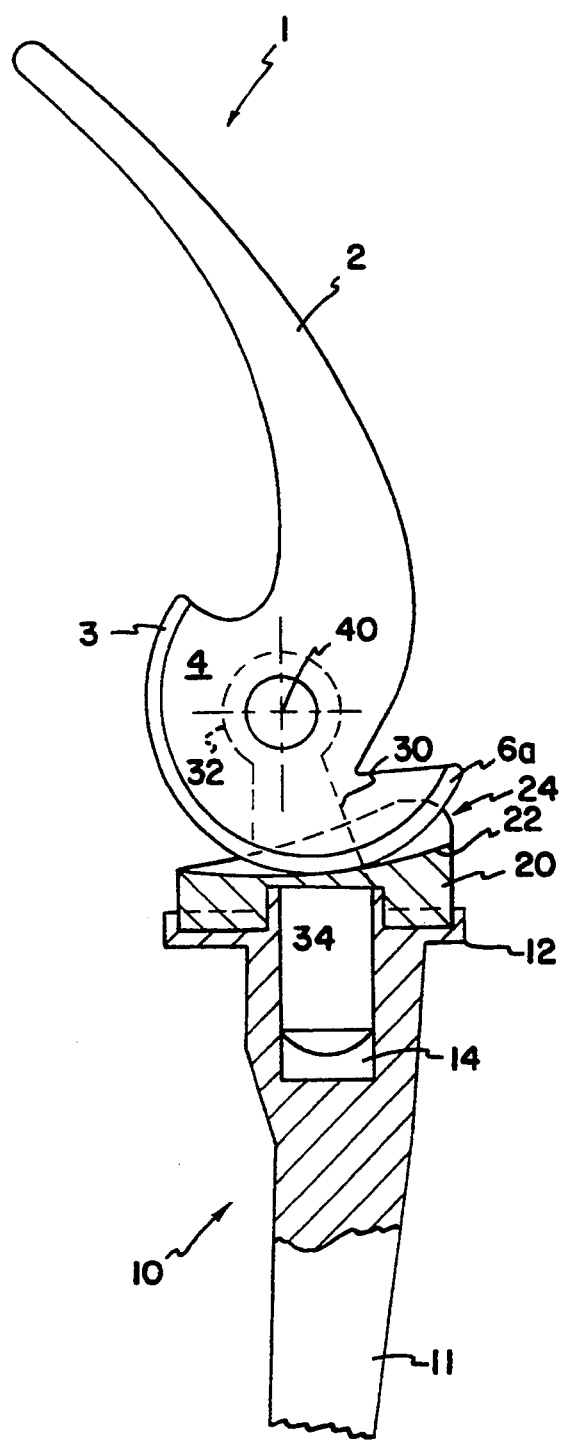
FIG. 1 shows a side view of the knee-joint endoprosthesis, partially in a cut.

The knee-joint endoprosthesis based on FIG. 1 consists of a femoral part 1, which has a shaft 2 for anchoring in the bone cavity of the human femur bone. Disposed at the lower end of the shaft 2 are two relatively thin-walled condylar pans 3, which, in the case of an implantation of the femoral part 1, should encompass the condyles of the natural femur bone. The two condylar pans 3 each have a lateral wall 4 running downwardly from the shaft. The two lateral walls 4 are joined with one another via an upper transverse wall 5, and form between them an intervening space 9, into which—in the pictured form of embodiment—projects the upper end of a connecting part 30 that is pivotably journaled on the femoral part by means of a transverse pin 40. Each lateral wall 4, at its end facing away from the shaft 2, passes over into a supporting wall 6 running outwardly away from the intervening space 9.

The femoral part 1 supports itself, via the support walls 6 of the condylar pans 3, on a tibial part 10, which carries a tibial plateau 20 made of plastic material. The tibial plateau 20 has, beneath the support walls 6 of the condylar pans 3, in the dorsal/ventral direction, a support area 22 adapted to each one of the support walls 6.

Running in the dorsal/ventral direction between the support areas 22 is a protuberance 24 that runs in the intercondyloid intervening space 9, and serves as a stop for a rotational movement of the femoral part 1 relative to the tibial part 10. The tibial plateau 20 is seated on a plate 12 that passes over toward the bottom into a shaft 11, which serves for anchoring the tibial part in the bone cavity of the natural tibia bone.

In the case of the axle-knee prosthesis represented, the connecting part 30 journaled in articulated fashion on the transverse pin 40 in the intervening space 9 with an eye 42, is coupled with the tibial part 10 such that the femoral part can execute a bending or pivoting movement on the tibial plateau about an—in the representation—essentially horizontal axis and, additionally, a rotational movement about an essentially vertical axis. For this purpose, the lower end of the connecting part 30 is constructed as a pin 34 that is guided in axially-displaceable fashion in a corresponding boring 14 in the tibial part.

FIG. 2 and FIGS. 3a to 3d show the femoral part 1 in a side view as well in the cuts IIIa to IIId. According to FIGS. 2 and 3a to 3d, the shaft 2 of the femoral part 1, at its lower end, passes over into two laterally-opened, condylar pans 3 that display, at a predetermined distance apart, downwardly-running lateral walls 4, between which is constructed an intervening space 9. The lateral walls 4 have at their lower ends, as can be obtained in particular from FIG. 2, a convexly-curved contour, and at their lower end pass over into support walls 6, which are directed outwardly and, as an approximation, form a surface of rotation about a support wall axis 8 that penetrates the lateral walls 4 of the condylar pans. Ventrally, the support walls each run into a patella tip 6a having a lesser curvature.

Figure 2:
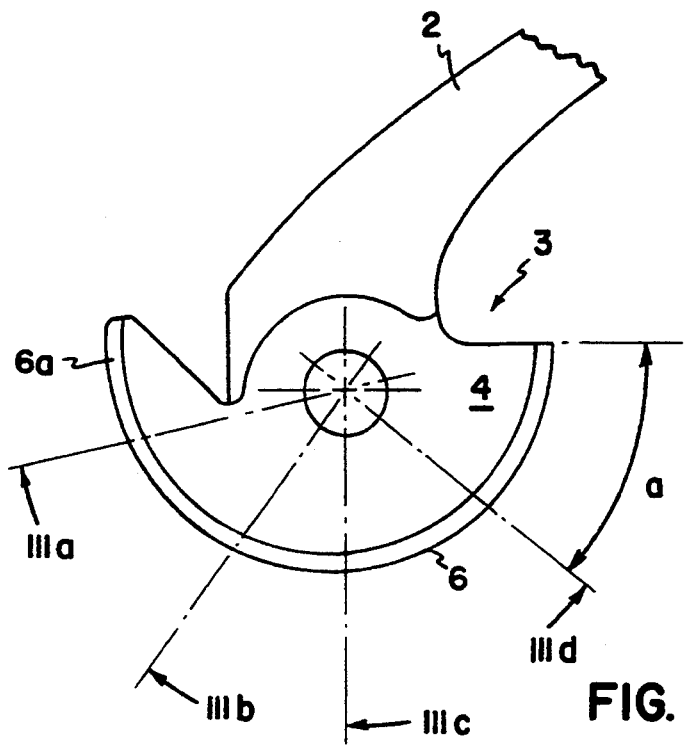
FIG. 2 shows a side view of the femoral part of the knee-joint endoprosthesis in accordance with FIG. 1.

As can, in particular, be obtained in FIGS. 3a to 3d, which reproduce the sections IIIa to IIId through the femoral part in accordance with FIG. 2, the condylar pans 3 display, at the transition 5 of the lateral wall 4 to the support wall 6, a recess 7 directed toward the inside of the pan, which widens the intercondyloid intervening space 9 to the extent that the patella (knee cap) can enter into the widened zone of entry 9a. The recess, as can be obtained from the sequence of FIGS. 3a to 3d, is thickest at the ventral beginning of the condylar pans, runs for a predetermined distance dorsally and decreases in depth dorsally. The recess 7 ends at a predetermined section of circumference before the ventral ends of the condylar pans 3, because this ventral end section, even in the case of strongest bending of the knee joint, is still fully supported on the support areas 22 of the tibial plateau 20, while the ventrally-adjoining region has pivoted itself free, upwardly away from the tibial plateau. The widened entry zone 9a of the intervening space 9, which has arisen through the mirrored, oppositely-lying recesses 9, can then accommodate the knee cap, whereby the ligamentous apparatus of the knee cap—in the case of stronger bending—can shorten and, therewith, relax. The contacting pressure exerted on the prosthesis by the knee cap—frequently the cause for difficulties in the region of the knee cap—is again reduced in this manner with stronger bending, the pattern of patella pressure on the condyles as a function of the bend angle being therewith better adapted to the natural conditions.

Figure 3A:
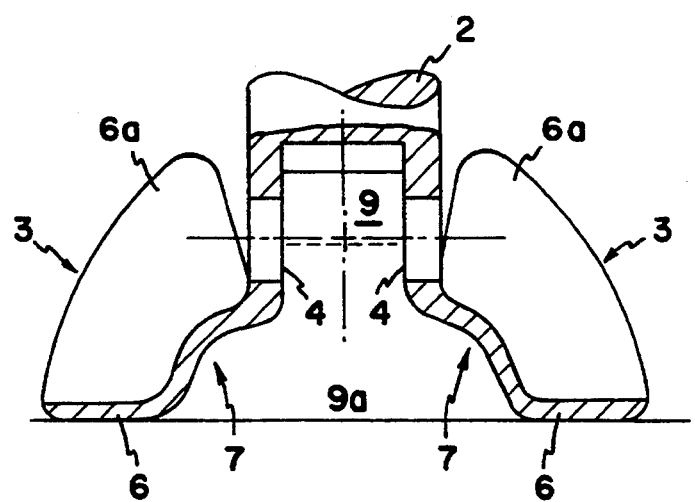
FIG. 3a show various cross sections through the condylar pans of to 3d the femoral part in accordance with FIG. 2.
Figure 3B:
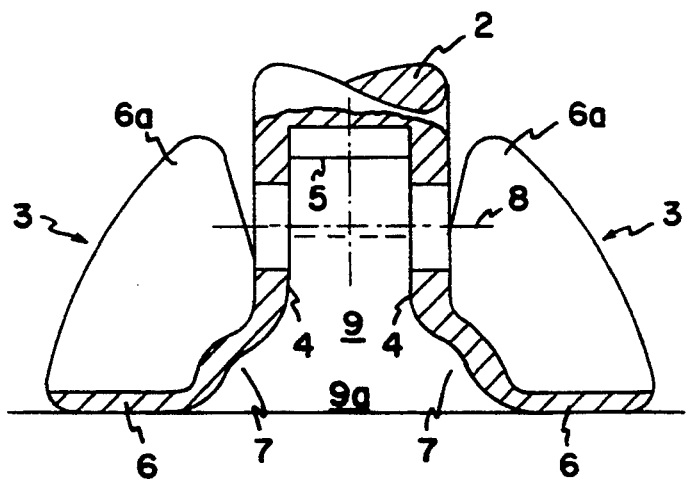
Figure 3C:
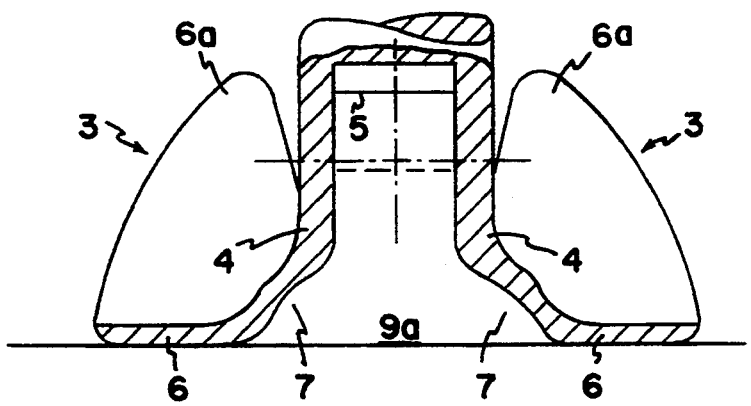
Figure 3D:
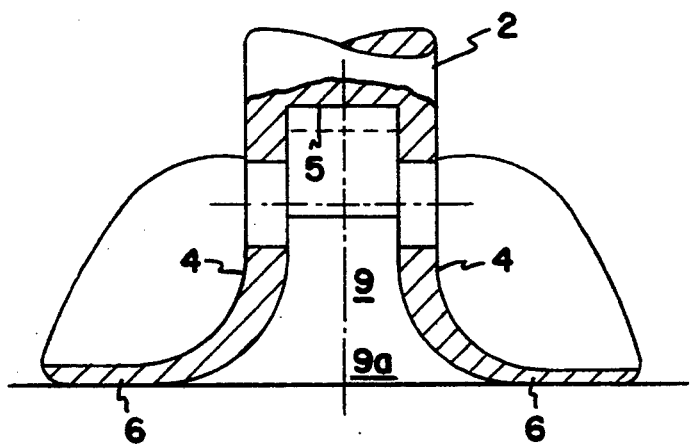
Figure 4:
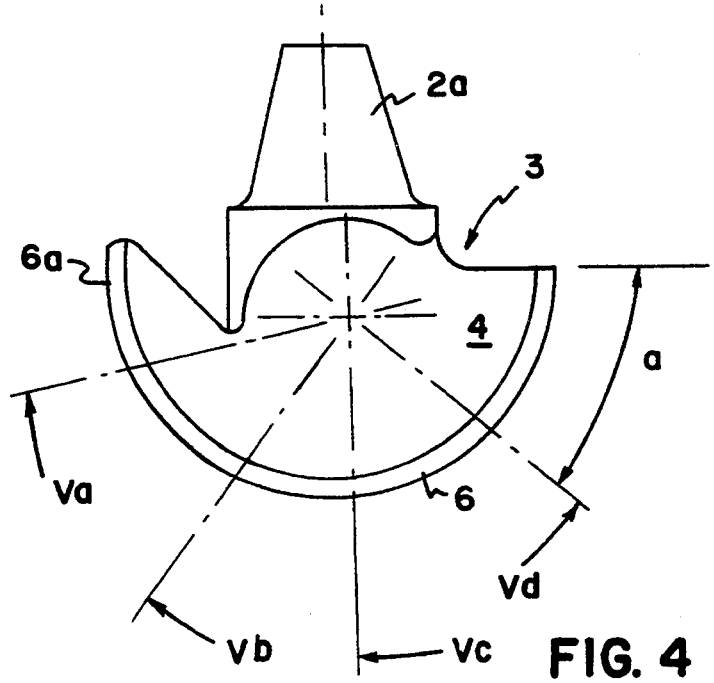
FIG. 4 shows a side view of the femoral part of a shaft-free, knee-joint endoprosthesis.
Figure 5A:
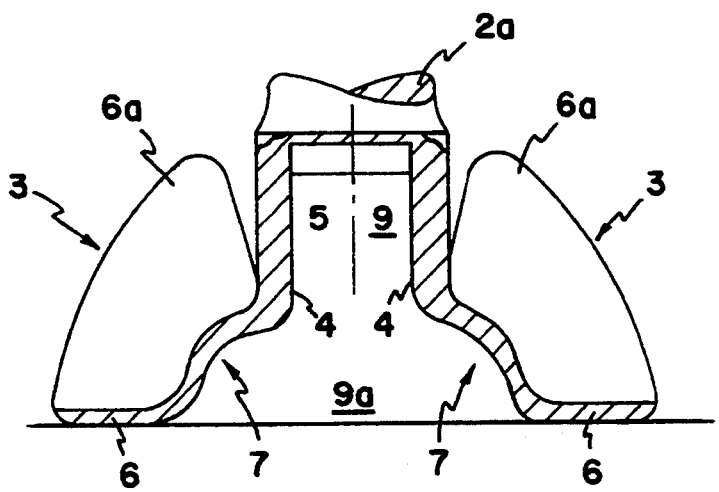
FIG. 5a show various cross sections through the condylar pans of to 5d the femoral part in accordance with FIG. 4.
Figure 5B:
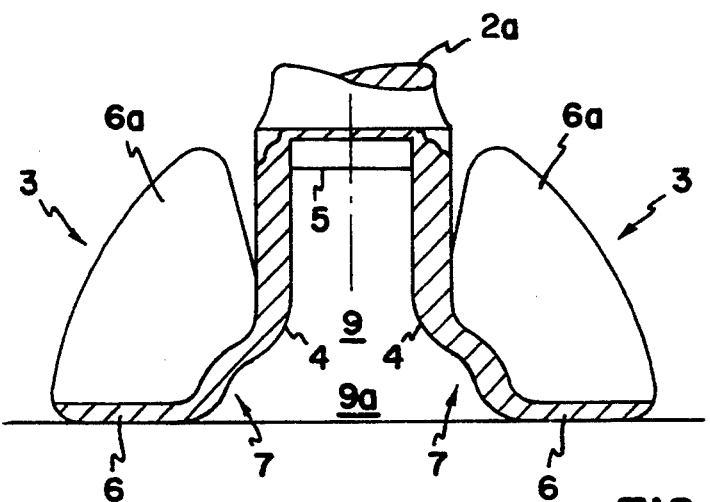
Figure 5C:
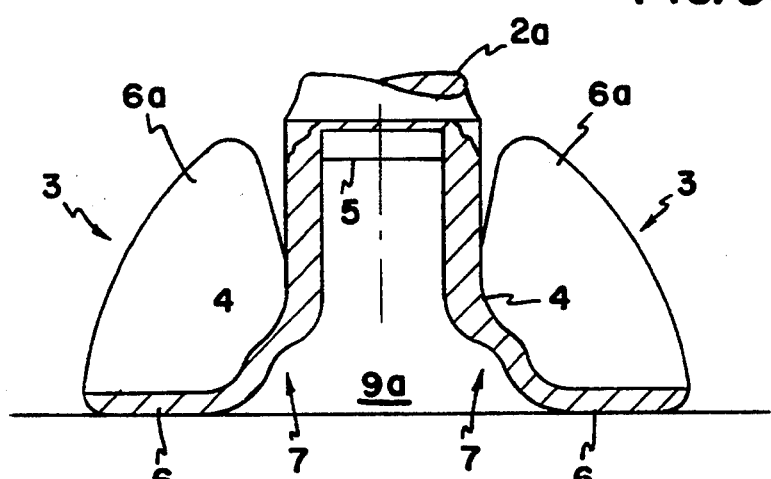
Figure 5D:
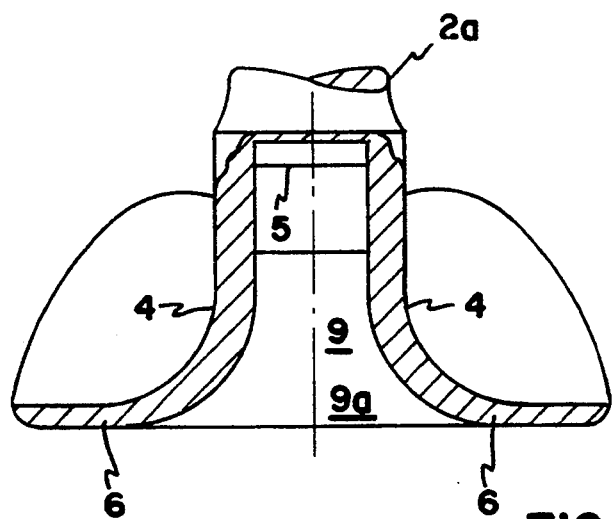

FIGS. 4 along with 5a to 5d show another form of embodiment of the invention which, to a great extent, corresponds to that of FIGS. 2 to 3d, with the same reference numbers being used for the same parts. In contrast to the form of embodiment based on FIGS. 2 to 3d, this form of embodiment, in place of the shaft 2 has a short anchoring pin 2a that serves for fixing the femoral part in the femur bone. The lateral walls 4a of the condylar pans do not have a transverse boring; the condylar pans 3a support themselves in axle-free fashion, i.e. without a transverse pin 40, on the tibial part 10.

In this form of embodiment of the invention also, the condylar pans 3a, ventrally at the transition of the lateral wall 4a to the support wall 6, has a recess 7 directed toward the inside of the pans. The depth of the recess 7 decreases in the dorsal direction. The recess 7 is dimensioned such that the knee caps, with strong bending movements, lie with their lateral zones lightly against the recessed surfaces of the condylar pans, and can be guided laterally.

I claim:

1. A knee-joint endoprosthesis, comprising a femoral part having, at a lower end, two condylar pans, and a tibial part having a tibial plateau, each condylar pan including a downwardly-running lateral wall, and a supporting wall running outwardly from the lateral wall for resting against the tibial plateau, the condylar pans display, ventrally at a transition of the lateral wall to the supporting wall, a recess directed toward inside of the pan, the recess being disposed at the transition of the lateral wall to the support wall, the recess providing a space for a patella which runs in the recess when the femoral and tibial parts of the prosthesis are flexed.

2. A knee-joint endoprosthesis according to claim 1, wherein the recess extends for a predetermined length from an anterior portion to a posterior portion of the femoral part.

3. A knee-joint endoprosthesis according to claim 1, wherein the recess is tapered in an anterior to a posterior direction so that the depth of the recess decreases in the dorsal direction.

4. A knee-joint endoprosthesis according to claim 3, wherein the depth of the recesses decreases to zero dorsally.

5. A knee-joint endoprosthesis according to claim 4, wherein the recess extends for a predetermined distance toward the lateral wall and the support wall.

6. A knee-joint endoprosthesis according to claim 5, wherein support areas of a tibial plateau display a bulge running ventrally/dorsally in correspondence to the recesses.

7. A knee-joint endoprosthesis according to claim 6, wherein a connecting means joins the femoral part and the tibial part for pivotal articulation, the connection means includes a connecting part that joins the femoral part and the tibial part with one another in articulated fashion.

8. A knee-joint endoprosthesis according to claim 7, wherein the connecting means has one end which extends into the recess and an opposite end rotatably coupled to a bore in the tibial part, wherein the connecting part projecting with one end into an intervening space between the lateral walls and the condylar pans, is joined in pivotable fashion with the femoral part by means of a transverse pin, and is rotatably journaled with a pin in a boring of the tibial part.

9. A knee-joint endoprosthesis according to claim 8, wherein the lateral walls of the condylar pans pass over into a common shaft for anchoring in the femoral bone.

10. A knee-joint endoprosthesis according to claim 9, wherein the tibial plateau is disposed at an upper end of a shaft.

11. A knee-joint endoprosthesis according to claim 10, wherein the lateral walls of the condylar pans connect with a common anchoring pin.

* * * * *